United States Patent [19]

Laumann, Jr.

[11] Patent Number: 4,911,616
[45] Date of Patent: Mar. 27, 1990

[54] MICRO MINIATURE IMPLANTABLE PUMP

[76] Inventor: Carl W. Laumann, Jr., 6926 301 Blvd., Sarasota, Fla. 34243

[21] Appl. No.: 145,542

[22] Filed: Jan. 19, 1988

[51] Int. Cl.$^4$ ............................................. F04B 17/00
[52] U.S. Cl. ..................... 417/413; 417/410
[58] Field of Search ............... 417/322, 413, 474, 410; 310/324, 309, 12; 346/140 PD

[56] References Cited

U.S. PATENT DOCUMENTS

| | | | |
|---|---|---|---|
| 3,264,998 | 8/1966 | Dingman | 417/474 X |
| 4,514,742 | 4/1985 | Suga et al. | 417/322 X |
| 4,520,375 | 5/1985 | Kroll | 417/410 X |

FOREIGN PATENT DOCUMENTS

| | | | |
|---|---|---|---|
| 48408 | 8/1984 | Japan | 417/413 |
| 48608 | 8/1986 | Japan | 417/322 |

*Primary Examiner*—Leonard E. Smith
*Attorney, Agent, or Firm*—Hugh D. Jaeger

[57] ABSTRACT

A microminiature pump for use in the eye or other location in the human body. The pump is fabricated from crystalline silicon using semiconductor fabrication techniques such as impurity diffusion and anisotropic etching. The pump utilizes a thin, etched, diaphragm which is actuated with electromagnetic or electrostatic forces, to provide the pumping action. Diaphragm or ball check valves at the inlet and outlet are also fabricated with semiconductor materials and techniques.

10 Claims, 6 Drawing Sheets

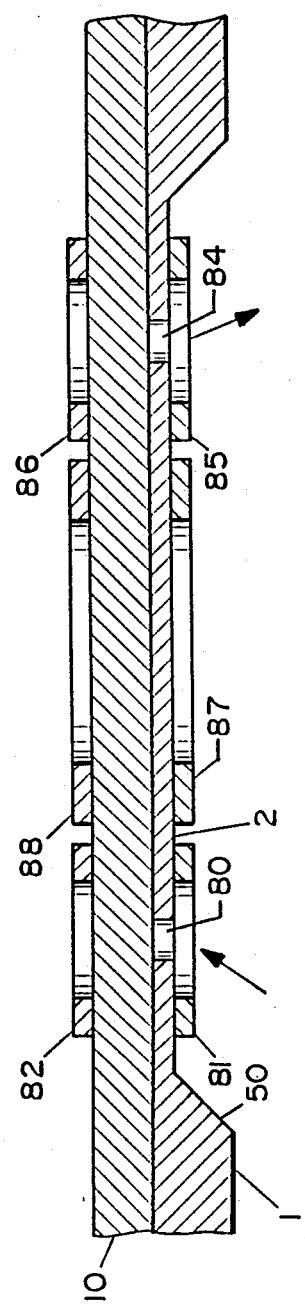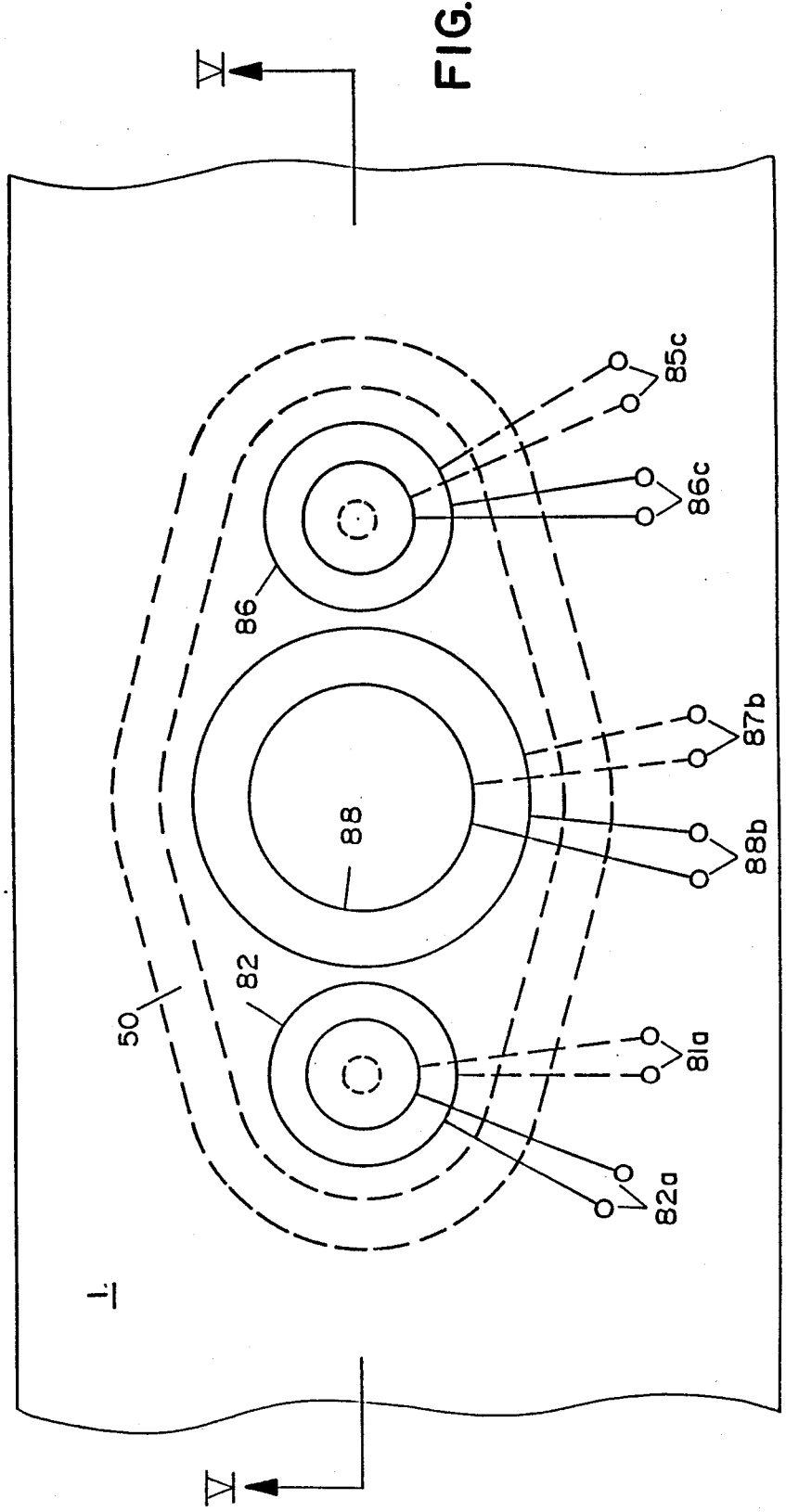

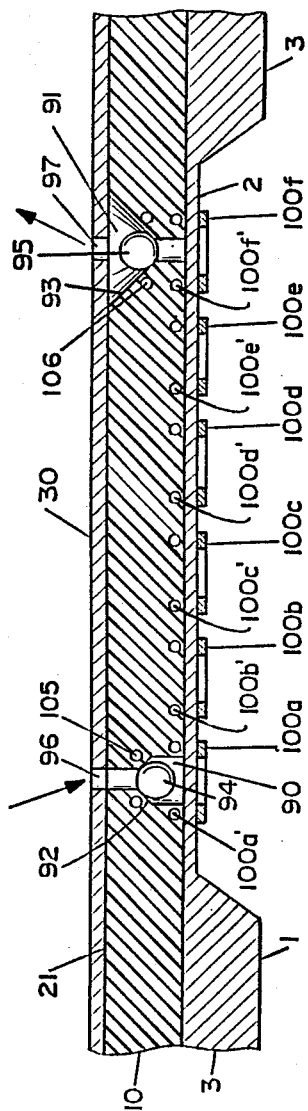
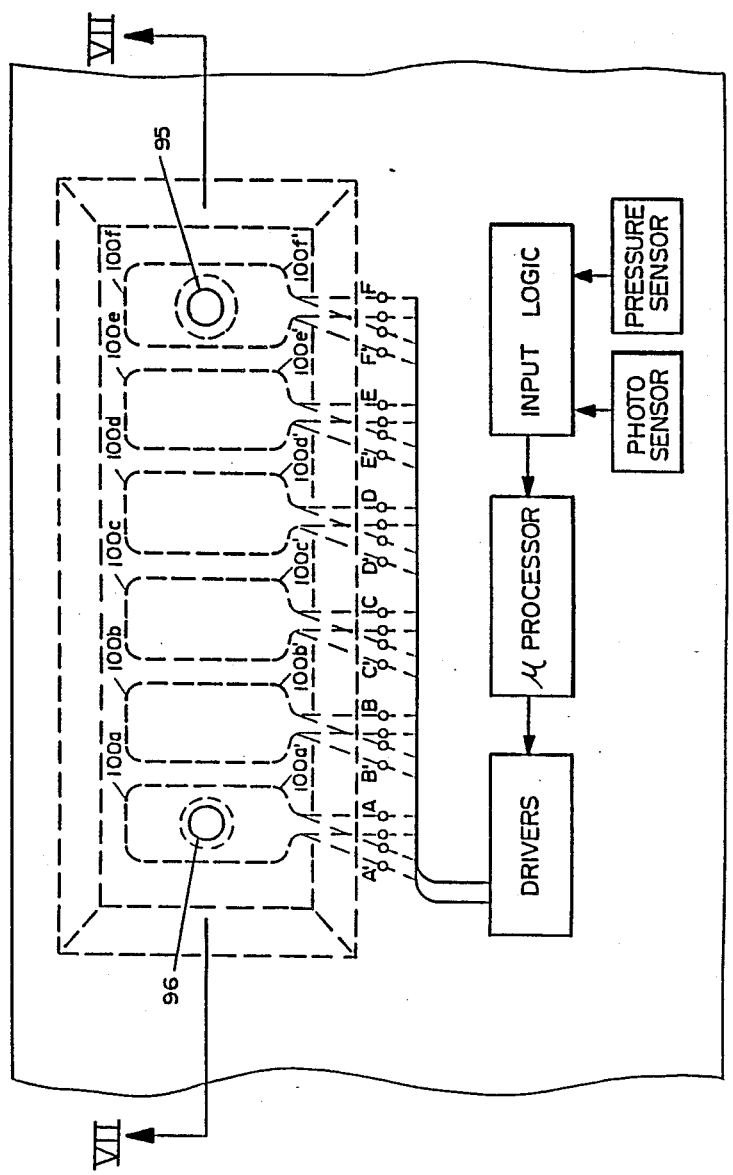
FIG. 7
FIG. 8

MICRO MINIATURE IMPLANTABLE PUMP

BACKGROUND OF THE INVENTION

1. Field of the Invention - The present invention relates to a microminiature pump suitable for implantation in a living body and particularly to an implantable pump which is compatible with microelectronic circuitry fabrication techniques and materials.

2. Description of the Prior Art - Great strides have been made in the miniaturization of electronic circuits and the attendant reduction of power required to operate such circuits has led to the development of implantable medical devices which operate for long periods of time, years in fact, without replacement of the battery.

Similar developments have taken place in the field of mechanical devices, where the application of semiconductor processing techniques has led to the development of transducers and actuators made from material such a crystalline silicon. Several devices of this type are described in a paper "Silicon Mechanical Devices" by James B. Angell, Stephen C. Terry and Phillip W. Barth, published in the Scientific American, Apr., 1983.

These two fields have been developing simultaneously and have led to smaller electronic circuits and smaller mechanical devices. Despite the significant developments in the respective fields, there has not been a comparable advance in the art which combines electronics and mechanics. Thus, the expected single chip combinations of microminiature mechanical devices with micro circuits have not been forthcoming, and, in their stead, various hybrid arrangements such as shown in the paper "Silicon Mechanical Devices" have been the rule. While hybrid devices represent an improvement, they do not represent the ultimate in small size or reliability since the discrete components must be larger than would be possible with a complete, integrated, device, and the additional electrical connections required are potential failure points.

The present invention relates to a fluid pump in which all circuits and all the mechanical aspects are implemented in semiconductor technology and no hybrid components are required. The pump can be of the diaphragm or peristaltic type in which the sole moving part is a very thin section of silicon actuated by either electrostatic or electromagnetic force. If desired, check valves at the input and the output have seats or a diaphragm which are fabricated from the same silicon wafer as used to fabricate the pump diaphragm. Where check valves of the ball variety are used, the balls are coated with conductive material to allow electrostatic or electromagnetic actuation.

By virtue of the small size, low power requirements and construction material, the pump is suitable for dispensing drugs and movement of body fluids such as found in the eye.

SUMMARY OF THE INVENTION

The general purpose of the invention is to provide a microminiature pump which is small enough to permit it to be placed at any desired location in the human body without adverse effects due to its size. Such pumps find use for the periodic dispensing of drugs at the optimum site within the body, for example, at the site of a tumor in the treatment of cancer or within such sensitive portions of the body as the brain and even the eye. The pump is operated and controlled with electronic circuitry and logic which is fabricated on the same silicon substrate and by the same processes as used to make the circuitry.

According to one embodiment of the invention, there is provided a silicon substrate having a first input valve and a second output valve with a communicating pump chamber having a diaphragm at one side. The diaphragm is sufficiently thin to allow flexing either by means of electromagnetic fields induced with windings on the diaphragm and a base member or by electrostatic forces resulting from charges applied to closely spaced plates on the diaphragm and the base member. The input and output valves may be of the ball-check type in which a circular ball is disposed within a valve chamber. The ball may be coated with a conductive material to allow it to be moved with electromagnetic or electrostatic forces. Instead of ball-check valves, diaphragm valves can be used, by creating an extension of the pump diaphragm or by fabricating discrete diaphragms for each valve.

Alternatively, the diaphragm may have an elongated, instead of circular, shape. In such an embodiment, the windings or plates are arranged to allow the diaphragm to be deflected to produce a wave, or peristaltic action on the fluid. This configuration has the advantage of being capable of operation without the use of check valves at the inlet and outlet ports. Since this version has no free moving parts and crystalling silicon does not suffer from fatigue, the mechanical life of such a pump is virtually infinite.

The selection of the embodiment will be dependent on the volume of fluid to be pumped, the viscosity of the fluid, the pressure required, the nature of the reservoir, the available power, the size and geometry of the space available on the silicon substrate and the length of time the device is to operate without failure or maintenance.

It is an object of this invention to provide a microminiature pump which is fully compatible with the semiconductor processing techniques and materials.

It is another object of this invention to provide a microminiature pump which is suitable for implantation into the most sensitive regions of the human body without substantial adverse physical or biologic reaction.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 5 is a partial cross-sectional view taken along the lines V—V of FIG. 6, showing a diaphragm pump according to the invention having diaphragm valves at the inlet and outlet ports.

FIG. 6 is a top view of the diaphragm pump of FIG. 5.

FIG. 7 is a partial cross-sectional view taken along the line VII—VII of FIG. 8, showing a peristaltic pump according to the invention having ball-check valves at the inlet and outlet ports.

FIG. 8 is a top view of the peristaltic pump of FIG. 7.

DESCRIPTION OF THE PREFERRED EMBODIMENTS

Figure 1:
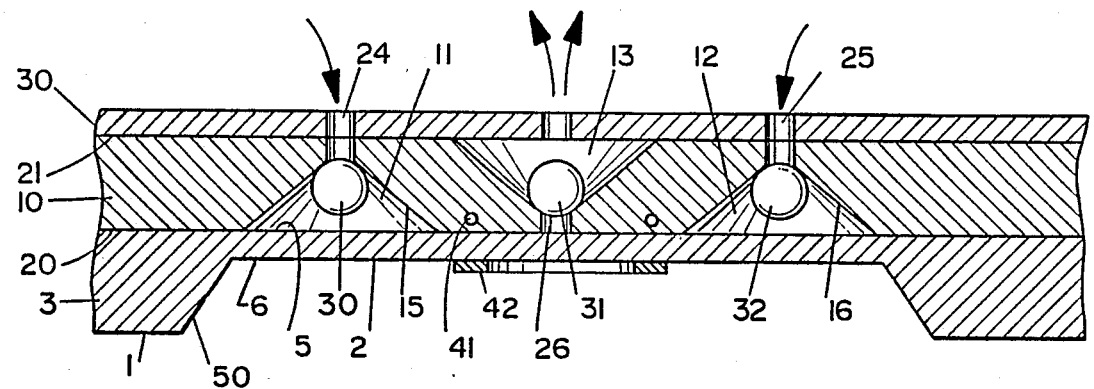
FIG. 1 is a partial cross-sectional view taken along the line I—I of FIG. 2, showing a diaphragm pump according to the invention having ball-check valves at the inlet and outlet ports.

With reference to FIG. 1, a base member 1 of single crystal silicon or like material, having has the characteristic that the etching rate may be altered by doping, has a extremely thin diaphragm portion 2 and a peripheral portion 3. The diaphragm portion is fabricated from a silicon wafer by an anisotropic etching process in accordance with known micromachining techniques such as described in the above mentioned paper. The silicon wafer is doped on one side with boron to a depth determined by the desired thickness of the diaphragm. The doping is made on the side 5, opposite the side 6 from which etching will occur. The doping is done to slow the etching process in the doped region. It has been found that anisotropic etchants, such as aqueous sodium hydroxide, aqueous potassium hydroxide, or the mixture known as EDP will not only etch in a fashion dependent on the orientation of the atomic planes of the silicon wafer, thereby avoiding the undercutting of the etch resist which results when isotropic etchants are used, it also etches at a rate which is dependent on the doping (level of impurities) in the material. The etching action of potassium hydroxide and EDP on silicon that is heavily doped with boron is much slower than undoped silicon or cilicon that is lightly doped with boron.

Thus, etching a wafer from a side which is not doped with boron, in the direction of the side heavily doped with boron to a depth of the desired diaphragm thickness, proceeds rapidly through the wafer until the doped region is reached. The etching process slows to a virtual stop, allowing great latitude in the timing of the etch without substantially affecting the ultimate thickness of the diaphragm.

It is even possible to develop diaphragms which are not coplanar with the rest of the wafer by growing an additional layer of exitaxial silicon over the surface of the silicon crystal after the doped layer is formed. This would allow the diaphragm to define a surface of a cavity between the diaphragm and the abutting cover member.

If any holes are to be later produced in the diaphragm, they will be masked off to prevent doping from occurring. An oxide coating is developed on the surface of the wafer and a coating of photoresist is applied to the oxide. A photographic mask which carries the pattern of the diaphragm is placed in contact with the photoresist and the wafer exposed to ultraviolet radiation. Then the wafer is rinsed in a developing solution which removes the exposed photoresist. The wafer is then placed in a bath of hydrofluoric acid which removes the oxide coating in the exposed areas to reveal the underlying silicon wafer. The remaining photoresist is then removed with hot sulfuric acid or similar solution, leaving a clean silicon wafer with portions masked by the oxide layer.

The etching process proceeds with an anisotropic etchant for a period of time sufficient to ensure that the undoped silicon is removed to the depth of the desired diaphragm thickness.

The valve plate 10 is also fabricated from crystalline silicon or like material using anisotropic etching processes to produce tapered walls in the valve ports. The inlet valves 11 and 12 have conical or pyramidal sloping walls 15 and 16 respectively. These walls are formed by anisotropic etching through holes in a mask on the surface 20 of the valve plate 10 and slope at an angle dependent on the crystal orientation of the plate 10. If the (100) surface is etched, the angle of the walls with respect to the surface will be 55 degrees. While it would be possible to simply continue the etching process from the side 20 until the opposite side 21 was reached, the size of the resulting hole in side 21 would be dependent on the etch rate, making it difficult to accurately control. It is preferable to heavily dope the side 21 with boron in all areas except those which are to be etched. Thus, when the anisotropic etch reaches the area of doping which surrounds ports 24 and 25, the etch continues in a relatively straight line, consuming only the undoped portion which defines the holes.

The outlet valve 13 is fabricated by the same process, that is, the region of port 26 is left undoped to provide a rapid etch when reached by the anisotropic etchant proceeding from side 21.

A valve cover plate 30 which may be silicon, glass or other suitable material is provided with holes which line up with the ports 24 and 25 of valve plate 10.

Assembly of the base member 1 with the valve plate 10 can be accomplished with conventional semiconductor bonding techniques. It is important only that the diaphragm portion 2 not be bonded to the valve plate 10, leaving the diaphragm free to be deflected away from the valve plate.

The valve cover 30 can be bonded to the valve plate 10 with conventional techniques. In the event that the valve cover is made of glass, the bonding may be accomplished by anodic bonding which is a well known electrostatic process sometimes called the Mallory process since it was developed by George Wallis and Daniel Pomerantz of the Mallory company.

Prior to bonding the base member, the valve plate and the valve cover, it is necessary to insert the balls 30, 31 and 32 into position. Depending on the particular application of the pump, it may or may not be necessary to bias the balls against their respective valve seats. In some applications, the liquid flow through the valves induced by diaphragm movement may be sufficient to provide satisfactory valve action. If this not adequate, the balls may be coated with conductive material such as gold and suitable conductive regions may be provided in the sloping walls of the valves. When these regions are electrically charged, the resulting electrostatic forces will be effective to attract or repel the balls. Since the normal fluid flow will be in the direction assisting the electrostatic force, very little additional force is required.

Alternatively, the balls may be biased with electromagnetic force provided by a winding made by a conductor in the region of the valve walls. Such a conductor could take the form of a diffused winding in the surface of the walls. The magnetic field resulting from current flow through the winding would induce a current in the conductive coating of the balls, causing the balls to move away from the winding.

The diaphragm motion is produced by a pair of windings 41 and 42, located on the valve plate 10 and diaphragm 2, respectively. When electrical current is passed through these windings to produce similarly poled electromagnetic fields, the resulting mechanical force pushes the diaphragm 2 away from the valve plate 10. The displacement of diaphragm 2 away from the valve plate 10 causes fluid to be drawn through the inlet valves 11 and 12 into the region between the diaphragm 1 and the valve plate 10. At the same time, it may be desirable to energize the plates or windings associated with the valves 11 and 12 to ensure that they are open and the winding or plate associated with valve 13 to ensure that it remains closed.

When the diaphragm has reached the point of maximum deflection, and the resulting pump chamber has filled with fluid, the signals to valves 11, 12 and 13 are reversed and the drive to the diaphragm windings 41 and 42 is either terminated or reversed, causing diaphragm 2 to revert to its normal, undeflected, position. The fluid previously drawn into the pump cavity is then expelled through the outlet valve 13.

Again, the preponderant portion of the energy required to operate the valves will be supplied by fluid flow.

Figure 2:
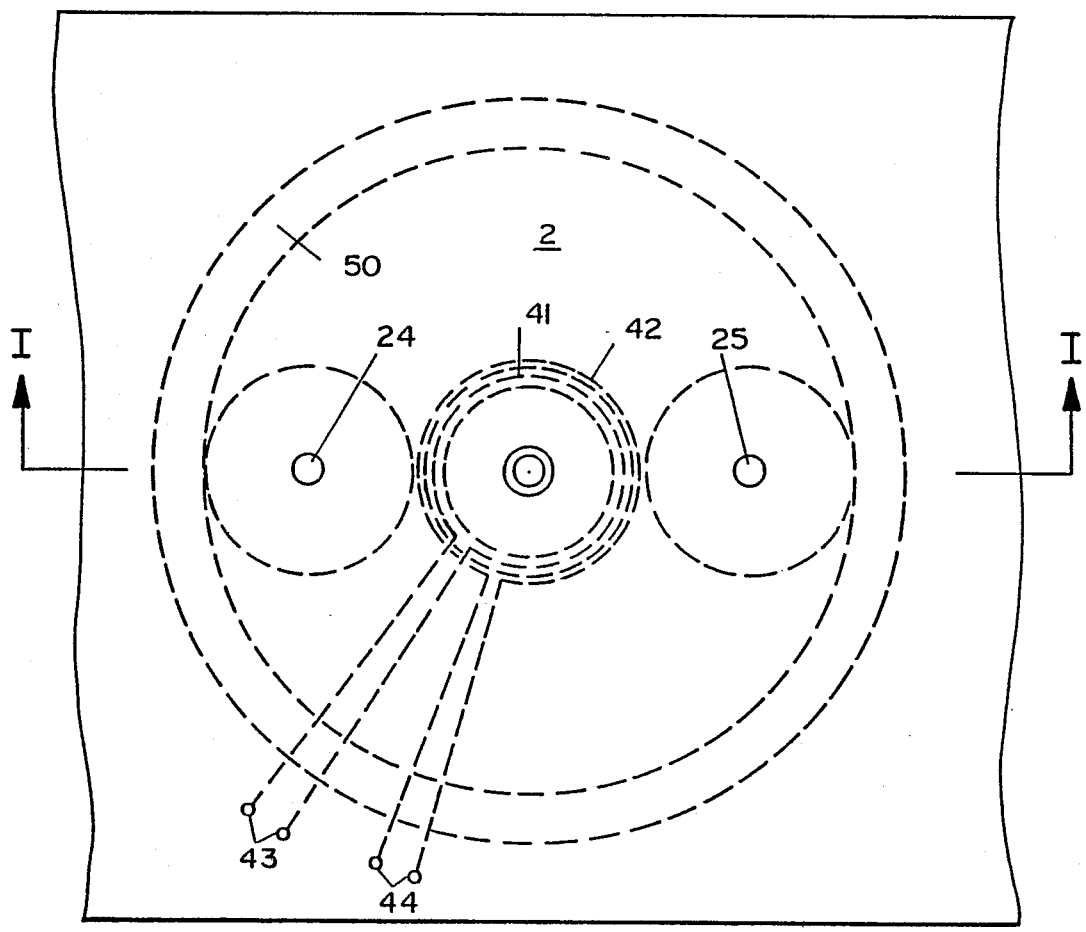
FIG. 2 is a top view of the diaphragm pump shown in FIG.1.

With reference to FIG. 2, which shows a top view of the pump of FIG. 1, the circular diaphragm 2 abuts angled side wall 50, which extends downwardly from surface 6 at a 55 degree angle. Inlet ports 24 and 25 are located near the periphery of diaphragm 2. The central portion of diaphragm 2 carries a diaphragm actuator winding 42 and the central portion of valve plate 10 includes an actuator winding 42. Terminals 43 and 44 connect to windings 41 and 42 respectively. When energized by similarly poled currents, the windings attract each other and cause the diaphragm 2 to be drawn against the valve plate 10. When oppositely energized, the windings repel each other and cause the diaphragm 2 to move away from valve plate 10.

It can be seen that the failure of any of the valves to operate properly does not result in leakage through the pump since the deenergized diaphragm seals the opening into the outlet valve. The fail-safe aspect is significant when the pump is used internally to dispense drugs.

The "real estate" on the silicon wafer required for the pump is only a small portion of that available on such wafers and the wafer can therefore be shared with conventional semiconductor devices such as transistors, diodes, photoelectric sensors, solar cells, radio frequency sensors, pressure sensors, microprocessors and data storage devices. For example, the terminals 43 and 44 may be directly connected to drive circuits energized in accordance with signals from a microprocessor. The microprocessor then operates under the control of a stored program which is modifiable by means of data entered via photo sensors or radio frequency sensors. This would enable the operation of the pump to be modified without direct physical connection to the pump, a prime requirement for a device which could be implanted deep within the human body or other inaccessible location.

Figure 3:
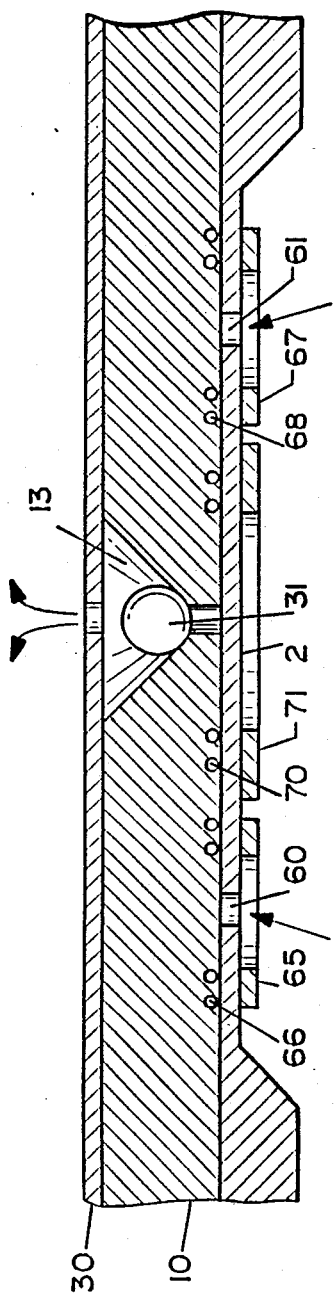
FIG. 3 is a partial cross-sectional view taken along the line III—III of FIG. 4, showing a diaphragm pump according to the invention having diaphragm valves at the inlet and a ball check valve at the outlet port.
Figure 4:
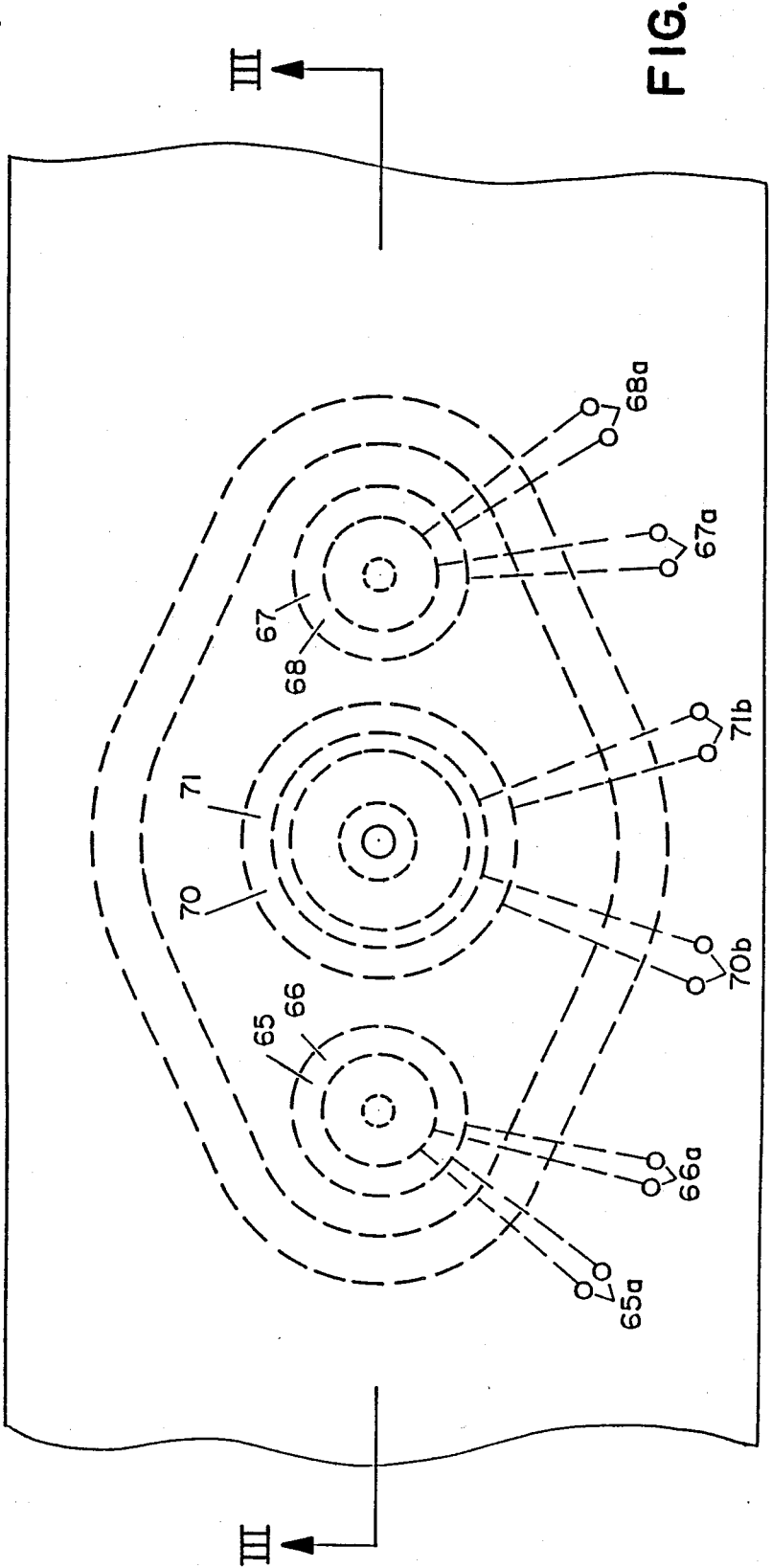
FIG. 4 is a top view of the diaphragm pump shown in FIG. 3.

The embodiment shown in FIGS. 3 and 4 is similar to that of the FIGS. 1 and 2 except that diaphragm valves are used at the inlet instead of ball check valves. This embodiment has the advantage of fewer mechanically free parts and therefore should be less likely to fail. It also retains the advantage of being fail-safe, in that failure of the pump does not result in leakage between the inlet and outlet.

The diaphragm 2, having an elongate or generally oval shape, is fabricated in the same fashion as previously described except that two or more inlet ports 60 and 61 are etched near the periphery of the diaphragm in the end regions thereof. Each inlet port has associated pairs of actuator windings 65, 66 and 67, 68, respectively. Windings 65 and 67 are affixed to the diaphragm while windings 66 and 68 are within valve plate 10. When energized with the appropriately poled currents, the windings operate to either repel the portion of diaphragm 2, adjacent inlet ports 60 and 61, from the valve plate 10 or to attract it thereto. Thus, the region of diaphragm 2 which lies adjacent to the ports 60 and 61 operates as a valve to either allow flow of fluid through ports 60 and 61 when that region of the diaphragm is spaced from the valve plate 10 or to prevent such flow when the region lies against the valve plate 10. It will be appreciated that the diaphragm 2 is sufficiently thin to allow the individual regions to flex without causing corresponding movement in other, spaced, regions.

In operation, the actuator windings 65–68, associated with the inlet ports 60 and 61, are first energized by signals applied to terminals 65a–68a, respectively, to open the ports. Subsequently, the actuator windings 70 and 71 are energized by signals applied to terminals 70b and 71ba to cause the central portion of diaphragm 2 to move away from valve plate 10. The movement of diaphragm 2 away from valve plate 10 causes fluid to be drawn through inlet ports 60 and 61 into the pump chamber.

After a short period of time to allow the pump chamber to fill with fluid, the actuator windings 65–68 are deenergized, allowing the diaphragm in the region of inlet ports to relax and close these ports. When the inlet ports are closed, the actuator windings 70 and 71 are deenergized or the flow of current in one winding reversed, causing the central portion of diaphragm 2 to move against the adjacent portion of valve plate 10. This causes the fluid in the pump chamber between valve plate 10 and diaphragm 2 to be expelled through the outlet valve 13. The cycle is then repeated.

The embodiment of FIGS. 5 and 6 uses diaphragm valves at both the inlet and outlet ports, thereby avoiding the need for any free moving mechanical parts such as the balls in the check valves of the earlier described embodiments. The base member 1 has an etched diaphragm 2, which can be fabricated as earlier described. The diaphragm has an inlet port 80, having associated diaphragm valve actuator winding 81, mounted on the diaphragm, and actuator winding 82, mounted on the valve plate 10. Energization of windings 81 and 82 with the appropriately poled signals causes motion of the diaphragm in the region of inlet port 80. Signals of one polarity cause the diaphragm to move away from valve plate 10 and open inlet port 80 and signals of the opposite polarity cause motion of the diaphragm toward the valve plate 10 to close inlet port 80, thereby providing the necessary inlet valve action.

Diaphragm 2 also has an outlet port 84, having associated diaphragm valve actuator winding 85, mounted on the diaphragm, and actuator winding 86, mounted on the valve plate 10. Energization of these windings with the appropriately poled signals causes the diaphragm in the region of outlet port 84 to move away from valve plate 10 and open outlet port 84 and signals of the opposite polarity cause motion of the diaphragm toward valve plate 10 to close outlet port 84, to provide the necessary outlet valve action for the pump.

A pair of pump diaphragm actuator windings, winding 87, mounted on diaphragm 2, and winding 88, mounted on valve plate 10 serve to move the central portion of the diaphragm for pumping action.

In operation, appropriately poled signals are first applied to input terminals 81a and 82a of inlet valve actuator windings 81 and 82, respectively, to move the portion of diaphragm 2 in the region of port 80 away from valve plate 10 and open the inlet valve and allow fluid to flow into the pump chamber through inlet port 80. At the same time or shortly thereafter, appropriately poled signals are applied to input terminals 87b and 88b of windings 87 and 88, respectively, to cause the central portion of diaphragm 2 to move away from valve plate 10 and draw fluid through inlet port 80 into the pump chamber between diaphragm 2 and valve plate 10. When diaphragm 2 is fully distendended, the signals applied to terminals 81a and 82a are either reversed, driving the portion of diaphragm 2 surrounding port 80 toward the valve plate 10, or simply terminated, allowing the diaphragm in the region of inlet port 80 to return to its normal unstressed position adjacent valve plate 10. In either case, the return of diaphragm 2 to a position abutting valve plate 10 causes the inlet port 80 to close, trapping the fluid drawn therethrough in the pump chamber.

At this point, an appropriately poled signal is applied to the terminals 85c and 86c of outlet valve actuator windings 85 and 86, respectively, to move the portion of the diaphragm in the region of the outlet port 84 away from valve plate 10 and open the outlet valve and allow the fluid in the pump chamber to flow out. The signals applied to terminals 87b and 88b of pump diaphragm actuator windings 87 and 88 are reversed to drive the diaphragm 2 toward valve plate 10 or simply terminated, allowing diaphragm 2 to return to its normal unstressed position, and, in so doing, expel the previously indrawn fluid through outlet port 84. When the diaphragm 2 has reached the position against the valve plate 10, the signals to terminals 85c and 86c are either reversed or terminated to position the portion of the diaphragm 2 surrounding outlet port 84 against valve plate 10 and thereby close the outlet valve.

It will be appreciated that the inlet and outlet valves include the portion of the diaphragm which surrounds the respective ports, the actuator windings and the cooperating portion of the valve plate.

The previous embodiments can be characterized as diaphragm pumps. The embodiment of FIGS. 7 and 8 is a peristaltic pump, in which the pumping action is provided by creating a "bulge" in an elongated chamber and moving the bulge from the inlet port to the outlet port. In this invention, although different terms are used to characterize the pumping action, both types utilize an etched, exceptionally thin diaphragm of crystalling silicon as the pumping element.

With specific reference to FIG. 7, a base member 1 of crystalline silicon or like material has an extremely thin diaphragm portion 2 surrounded by a peripheral portion 3. As can be seen from the top view of FIG. 8, the diaphragm has an elongate, generally rectangular shape. The diaphragm lies against the valve plate 10 which contains an inlet valve 90 and an outlet valve 91. Each of the valves 90 and 91 is of the ball check type having a tapered valve seat 92 and 93, respectively. Ball elements 94 and 95 cooperate with the valve seats 92 and 93 to allow flow only in the inward direction in the case of valve 90 and in the outward direction in the case of valve 91.

The diaphragm 2, the valve seats 92 and 93 together with the inlet port 96 and outlet port 97 are fabricated by an anisotropic etch process as previously described. Similarly, the base member 1, the valve plate 10 and the valve plate cover 21 are bonded as previously described, leaving the area between the diaphragm 2 and the valve plate 10 unbonded so that the diaphragm is free to move.

A plurality of actuating means comprising pairs of electrical windings 100a—100a', 100b—100b', 100c—100c', 100d—100d', 100e—100e', 100f—100f' are disposed in lengthwise fashion along the diaphragm 2. The sequence of windings 100a—100f is mounted on diaphragm 2. A corresponding sequence of windings 100a'—100f' is mounted on valve plate 10 in closely spaced opposition to the windings on diaphragm 2. The windings on valve plate 10 and diaphragm 2 can be in the form of diffusion formed conductors or discrete plating and terminals A-F and A'-F' respectively connected to the windings 100a-100f and 100a'-100f' as shown in FIG. 8.

A pair of actuator windings 105 and 106, imbedded in the sloping walls of the valve seats 92 and 93 provide means for controlling the position of the balls 94 and 95, respectively. Alternatively, the windings 10 and 106 may be used as plates for the introductionof an electrostatic charge which causes the motion of balls 94 and 95.

Operation of the peristaltic version of the pump begins with the opening of inlet valve 96 and the movement of the portion of the diaphragm actuated by the windings 100a and 100a'. When the inlet valve is opened and the diaphragm actuated by windings 100a and 100a', the resulting movement of the diaphragm 2 away from valve plate 10 causes fluid to be drawn through the inlet valve 96 into the pump cavity formed by the displaced diaphragm.

With the inlet valve still open and the windings 100a and 100a' still energized, the windings 100b and 100b' are energized to displace the portion of diaphragm 2 actuated by these windings. After the portion of diaphragm 2 actuated by the windings 100b and 100b' has reached the point of its maximum displacement, the actuating windings 100a and 100a' associated with the diaphragm and winding 105 associated with the inlet valve are deenergized, causing the inlet valve 96 to close and the portion of the diaphragm 2 actuated by the windings 100a and 100a' to move back against the valve plate 10. At the same time, tee windings 100c and 100c' are energized.

At this point both the inlet and outlet valves are closed and there is a fluid filled "bulge" in the diaphragm at the point where actuator winding 100b—100b' and 100c—100c' abut. This fluid filled bulge is now moved lengthwise along the diaphragm by subsequent sequential energization of the windings 100d—100d' through 100f—100f'.

Figure 11:
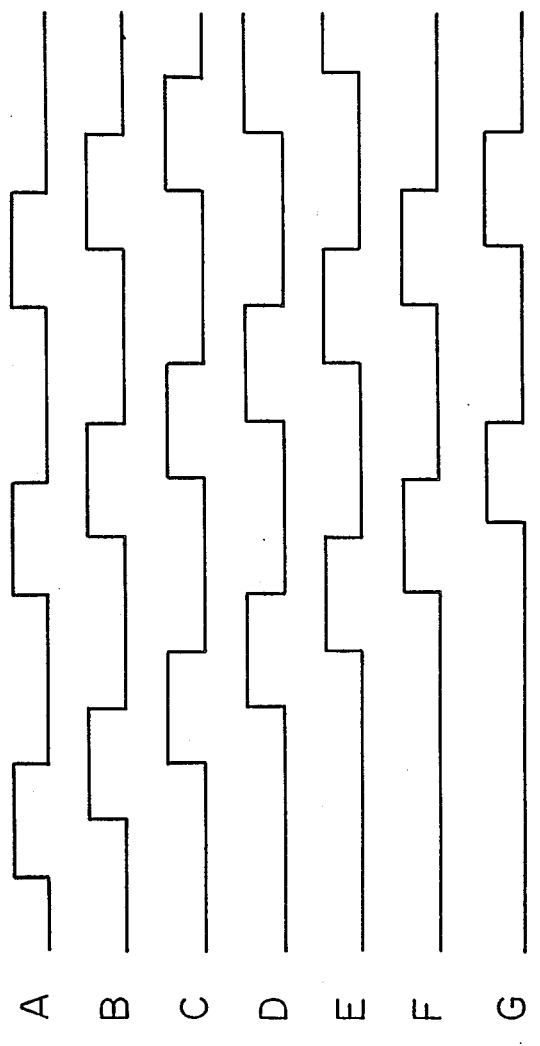
FIG. 11 is a timing diagram showing the wave forms of the signals used to energize the electrical actuators for the pumps of FIGS. 1-10.

FIG. 11 is a timing diagram showing the fashion in which the actuator windings are energized. The inlet valve is energized to be opened at the same time as windings 100a—100a'. The outlet valve is energized to be opened at a time shown in the line G, and closed at a point subsequent to the deenergization of windings 100f and 100f' (the timing line F). The timing line A corresponds to the signal applied to the terminals A and A' associated with windings 100a and 100a'. Similarly, timing line B corresponds to the signal applied to terminals B and B' associated with windings 100b and 100b'.

As shown in FIG. 8, the electronic components necessary to develop the drive signals can be fabricated on the same silicon crystal as the pump itself. Such components would include drivers for the individual actuator windings associated with the diaphragm and valves, a microprocessor having data storage capability to store a control program and commands issued from a remote source, photosensors for transmitting information to the microprocessor where the pump is located in a location where light can be used for this purpose, for example, the eye, pressure sensors to determine the output pressure of the pump or the reservoir into which it is pumping and other semiconductor devices.

Figure 9:
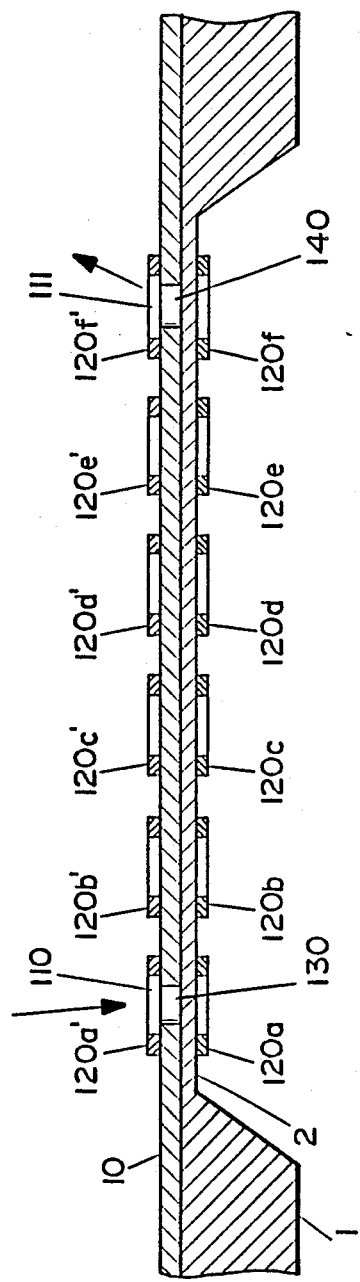
FIG. 9 is a partial cross-sectional view taken along the line IX—IX of FIG. 10, showing a peristaltic pump according to the invention having diaphragm valves at the inlet and outlet ports.

FIG. 9 shows a peristaltic pump in which both the inlet valve and the outlet valve are of the diaphragm type. The absence of free moving mechanical parts such as the check valve balls tends to make the pump more reliable and results in longer life.

Figure 10:
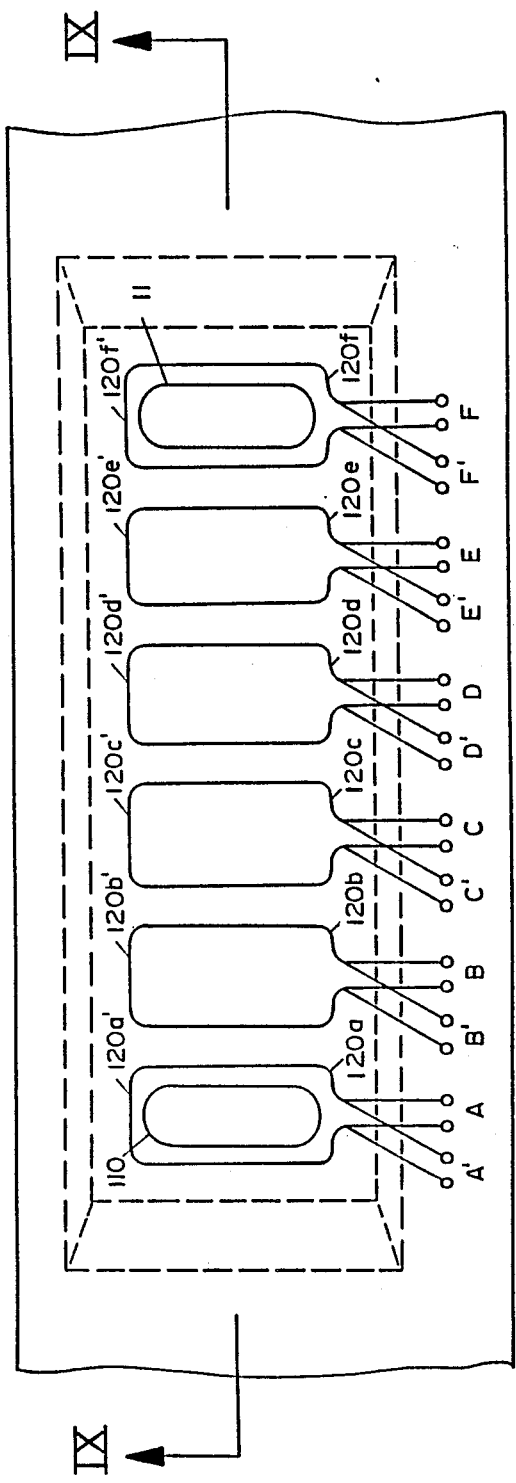
FIG. 10 is a top view of the peristaltic pump of FIG. 9.

The base member 1 has a very thin diaphragm portion 2 which is fabricated by an anisotropic etch process as previously described. The diaphragm 2 has an elongate rectangular shape as shown in FIG. 10. A valve plate 10 has an inlet port 110 and an outlet port 111. The valve plate is affixed to the base member through conventional semiconductor techniques, leaving the diaphragm portion 2 unbonded and free to move. Inlet valve actuator winding 120a, mounted on the diaphragm 2 and winding 120a', mounted on the valve plate 10, are positioned to move the portion of diaphragm 2 which abuts inlet port 110. When these windings are energized with the appropriately poled currents to develop opposing magnetic fields, the diaphragm 2 in the vicinity of the inlet port 110 will flex and move away from the valve plate 10, thereby opening the inlet valve 130 comprising the inlet port 110 and the abutting portion of diaphragm 2. When the inlet valve 130 is open, fluid is drawn through port 110 into the pump chamber formed between the displaced diaphragm 2 and valve plate 10.

With the windings 120a and 120a' still energized, the windings 120b and 120b' are energized to displace the portion of diaphragm 2 actuated by these windings. As this portion of the diaphragm is displaced it enlarges the pump chamber and causes still more fluid to be drawn through inlet port 110 into the pump chamber between diaphragm 2 and valve plate 10. The windings 120a and 120a' are then deenergized, causing the portion of diaphragm 2 adjacent the inlet port 110 to move back to its rest position against valve plate 10, thereby closing the inlet valve 130. At the same time, windings 120c and 120c' are energized, causing the fluid trapped in the pump chamber to move into the region defined by the energized windings 120b, 120b' and 120c, 120c'.

The pump cycle continues in this fashion, with the windings energized in the sequence shown in the timing diagram of FIG. 11.

The signal which energizes the respective windings 120d and 120d' is that represented by wave form D of FIG. 11. Similarly, windings 120e and 120e' are energized by a signal which is represented by wave form E. The signal which energizes the outlet valve actuator windings 120f and 120f' is represented by wave form F.

It will be appreciated that variations in the signals used to energize the windings are possible without departing from the scope of the invention. For example, it would be possible to increase the volume of fluid delivered by the pump by energizing more of the windings before the inlet valve is closed. This would have the effect of increasing the size (volume) of the pump chamber.

The minimum dimensions of the pump will be determined by the particular application and are limited only by the volume of fluid required to be delivered. The limited capacity of the smaller sizes is in fact an advantage in many applications since it permits very precise metering of the fluid.

In some applications it may be desirable to use the pump to maintain a precise fluid pressure. It is possible to incorporate a conventional semiconductor pressure transducer as a part of the control loop for the pump. Since such transducers are fabricated with the same semiconductor processing techniques as the pump, it is possible to incorporate such transducers in the same wafer or chip as the pump itself with the advantages of increased reliability and smaller size.

The various embodiments have been described with actuators of the electromagnetic variety. The windings on the diaphragm and base member can be replaced with simple electrostatic plates and the plates simply charged with the appropriate voltages to cause the desired movement of the valves and diaphragm. The voltages required to operate an electrostatic actuator system will be higher than generally required for the electromagnetic version. While such voltages are not conveniently obtainable directly from batteries, they are easily obtained with conventional circuitry which can be fabricated directly on the same wafer or chip as the pump itself. The wave form of the electrostatic drive signals will be essentially the same as shown in FIG. 11.

In the case where corrosive fluids are to be pumped, it is possible to passivate the surfaces of the pump which come into contact with the fluid. An oxide coating will be adequate in most situations but a coating of gold or similar material may sometimes be necessary.

The pump may be powered from conventional batteries since the consumption of power will be very low. Rechargable batteries can also be used since the circuitry for intercepting energy for recharging can be easily incorporated on the semiconductor wafer or ship used to fabricate the pump. In the case where the pump is positioned near the surface of the body, infrared or even visible light can be used for recharging. The light would be projected onto solar cells incorporated into the chip. Alternatively, where the pump is located deeper within the human body, radio frequency energy can be used and the intercepted energy can be rectified with diodes incorporated into the chip.

The use of an alterable storage unit on the semiconductor chip allows the control algorithm for the pump to be modified even after the pump is implanted. The use of a simple radio frequency detector and conventional radio frequency signalling techniques would allow the program to be altered to suit existing conditions. Where the pump is located in the eye or other site accessible to visible light, a simple optical device can be used to reprogram the device.

While the embodiments of FIGS. 7, 8 and 9, 10 are described as peristaltic pumps, they can easily be operated as diaphragm pumps by changing the timing and wave form of the signals applied to the actuator windings. For example, in the embodiment of FIGS. 7 and 8, simultaneously energizing the actuator windings 100$b$, 100$b$' through 100$e$, 100$e$' causes the elongate diaphragm to move as an entity, similar in fashion to the earlier described diaphragm pump of FIGS. 1 and 2.

Various other modifications can be made to the present invention without departing from the apparent scope thereof.

I claim:

1. A microminiature pump comprising:
   a. a base member of crystalline material doped to produce selective etching rates when exposed to etchants;
   b. an etched diaphragm portion of said base member, doped to produce a slower etching rate than the portion removed by etching, partially defining a pump chamber and having an electrically operated first actuating means affixed thereto;
   c. an inlet valve, of the same type of crystalline material as said base member, in fluid communication with said pump chamber for controlling the flow of fluid into said pump chamber;
   d. an outlet valve, of the same type of crystalline material as said base member, in fluid communication with said pump chamber for controlling the flow of fluid out of said pump chamber.

2. A pump device according to claim 1 having a valve plate of crystalline material doped to produce selective etching when exposed to etchants, said valve plate positioned adjacent said diaphragm and having said inlet valve and said outlet valve integral therewith.

3. A pump device according to claim 1 further including second and third electrically operated actuating means for said inlet valve and said outlet valve respectively.

4. A pump device according to claim 3 wherein at least one of said actuating means includes an electromagnetic winding.

5. A pump device according to claim 3 wherein at least of said actuating means includes electrostatic plates.

6. A pump device according to claim 3 wherein said valves each include an electrically actuated ball.

7. A microminiature pump comprising:
   a. a base member of crystalline material doped to produce selective etch rates when exposed to etchants;
   b. an elongated etched diaphragm portion of said base member partially defining a pump chamber and having electrically operated first and second actuating means affixed thereto;
   c. an etched inlet port in said diaphragm portion adjacent a first end thereof;
   d. an etched outlet port in said diaphragm adjacent a second, opposite, end thereof;
   e. said first actuating means including spaced elements disposed along the length of said diaphragm for deflection thereof and adapted to be selectively energized to induce a peristaltic wave within said pump chamber progressing from said inlet port to said outlet port.

8. A pump device according to claim 7 further including electrically operated second and third actuating means affixed to said diaphragm adjacent said inlet and outlet ports respectively.

9. A pump device according to claim 7 wherein at least one of said actuating means includes an electromagnetic winding.

10. A pump device according to claim 7 wherein at least one of said actuating means includes electrostatic plates.

* * * * *